(12) United States Patent
Schecter

(10) Patent No.: US 8,209,012 B2
(45) Date of Patent: Jun. 26, 2012

(54) MECHANICAL INDICATORS FOR INDIVIDUALLY ADAPTING THERAPY IN AN IMPLANTABLE CARDIAC THERAPY DEVICE

(75) Inventor: Stuart O. Schecter, Great Neck, NY (US)

(73) Assignee: Pacesetter, Inc., Sylmar, CA (US)

( * ) Notice: Subject to any disclaimer, the term of this patent is extended or adjusted under 35 U.S.C. 154(b) by 792 days.

(21) Appl. No.: 12/333,157

(22) Filed: Dec. 11, 2008

(65) Prior Publication Data

US 2010/0152796 A1 Jun. 17, 2010

(51) Int. Cl.
*A61N 1/365* (2006.01)
(52) U.S. Cl. .................................. 607/19; 607/17
(58) Field of Classification Search ............... 607/4, 17, 607/19
See application file for complete search history.

(56) References Cited

U.S. PATENT DOCUMENTS 7,610,089 B1 * 10/2009 Rodriguez et al. ............. 607/19

* cited by examiner

*Primary Examiner* — Carl H. Layno
*Assistant Examiner* — Jon-Eric C. Morales

(57) ABSTRACT

A system with an implantable cardiac stimulation device having an implantable stimulation generator, at least one implantable lead adapted for connection to the implantable stimulation generator and further adapted for at least one of sensing physiologic activity and delivery of therapy, memory, and a controller in communication with the memory and with the at least one implantable lead and stimulation generator. The controller is configured to automatically evaluate a patient's physiologic status and selectively induce delivery of therapeutic stimulation under variable timing parameters. The system also has a measurement system adapted to measure at least one of strain and velocity of myocardial tissue and is adapted to evaluate strain and/or velocity measures and adjust the variable timing parameters of the implantable stimulation device to increase mechanical synchrony of the myocardial tissue.

17 Claims, 8 Drawing Sheets

MECHANICAL INDICATORS FOR INDIVIDUALLY ADAPTING THERAPY IN AN IMPLANTABLE CARDIAC THERAPY DEVICE

BACKGROUND OF THE INVENTION

1. Field of the Invention

The invention relates to the field of implantable cardiac stimulation devices and more particularly to evaluating one or more measures of mechanical physiologic activity for individually optimizing or adapting therapy delivery provided by an implantable cardiac stimulation device.

2. Description of the Related Art

Numerous people suffer from physical ailments affecting their heart function. Patients having diseased myocardium often exhibit impairment of the normal physiologic conduction system, myocardial stunning, hibernation, and/or myocardial necrosis. Of these symptoms, myocardial stunning, hibernation, and necrosis generally lead to hypocontractility of the cardiac muscle. Many patients also exhibit reduced cardiac output as a secondary symptom of a lack of myocardial contractility, impaired conduction, and/or deficiencies in the synchronicity of cardiac depolarization/repolarization. These factors generally result in impaired systolic and/or diastolic function which results in the commonly named congestive heart failure (CHF) or simply heart failure (HF).

Accordingly, a variety of therapies, including therapies automatically provided by therapeutic devices, have been developed and continue to be further developed for treatment of patients, including patients suffering from HF. One particular category of therapy which has been developed is provided by implantable cardiac stimulation devices. Such cardiac stimulation devices are frequently configured to be implanted in order to provide long term automatic monitoring of the patient's condition and to generate and deliver therapeutic cardiac stimulation as indicated. Implantable cardiac stimulation devices have been developed to monitor and provide therapy independently to multiple locations of the patient's heart, including multiple chambers of the patient's heart.

One particular category of implantable cardiac stimulation devices includes the ability to monitor activity in and selectively deliver therapy to both of the patient's ventricles. This is frequently referred to as bi-ventricular or bi-V therapy. Implantable cardiac stimulation devices configured for bi-ventricular stimulation can be further configured to provide cardiac resynchronization therapy (CRT). CRT refers to modes of therapy which strive to restore a more closely normal synchronization between the patient's right and left ventricles.

While CRT is as yet not effective with all patients suffering from HF, for many HF patients, CRT can improve the overall pumping effectiveness of an HF patient and thereby improve their quality of life. In at least certain patients, CRT can at least partially compensate for conduction/stimulation deficiencies to thereby improve synchronization of the electrical stimulation of the myocardium and to at least partially compensate for myocardial tissue having impaired contractility.

While CRT has been shown to provide valuable benefits to certain HF patients, there remains a sizeable portion of the HF population that has been non-responsive or at best less responsive to existing CRT systems and algorithms. Thus, it will be appreciated that there exists needs for improved systems and methods of delivering cardiac therapy both to improve the efficacy for patients who have exhibited positive response, as well as to provide new types of therapy for those patients who have exhibited less beneficial response.

HF, for example, is often a progressive condition and can manifest in different disease conditions. Evaluation of the progression of disease conditions and the particular physiologic manifestations in an individual patient are important to improving therapy delivery, particularly where the condition is progressing and/or involves localized impairment. Thus, there is an ongoing need for systems of more accurately evaluating a patient's condition and providing appropriate indications for any changes in therapy. It would be beneficial to provide improved systems and methods of providing therapy that would be generally compatible with existing hardware platforms. It would be further advantageous to provide innovative systems and methods of providing therapy that would be compatible with improved hardware platforms.

SUMMARY OF THE INVENTION

Certain aspects of the invention involve, at least partially, evaluating indicators of mechanical activity of the patient's heart. Mechanical indicators can include strain measurements and/or velocity measurements. Mechanical indicators can also include electrical impedance which is indicative of the time varying changes in myocardial impedance associated with the cyclical contraction/relaxation of cardiac tissue as well as the cyclical intake and expelling of relatively low bulk resistivity blood.

In certain implementations, mechanical indicators can be obtained at least partially from externally arranged ultrasonic imaging equipment. Measures can be made of multiple regions of interest (ROI) to provide information on regional or localized conditions. Impedance measurements can be made with externally arranged impedance sensors and/or via an implantable therapy device configured for impedance sensing.

One embodiment includes a therapeutic stimulation system comprising an implantable cardiac stimulation device comprising an implantable stimulation generator, at least one implantable lead adapted for connection to the implantable stimulation generator and further adapted for at least one of sensing physiologic activity and delivery of therapy, memory and a controller in communication with the memory and with the at least one implantable lead and stimulation generator and configured to automatically evaluate a patient's physiologic status and selectively induce delivery of therapeutic stimulation under variable timing parameters and a measurement system adapted to measure at least one of strain and velocity of myocardial tissue and wherein the system is adapted to evaluate the at least one of strain and velocity measures and adjust the variable timing parameters of the implantable stimulation device to increase synchrony of the at least one of strain and velocity of myocardial tissue.

Another embodiment includes a method of adjusting therapy delivery in an implantable cardiac stimulation device, the method comprising providing therapeutic cardiac stimulation to a patient via an implantable cardiac stimulation device operating under a set of variable timing parameters, measuring at least one of strain and velocity of the patient's myocardial tissue, evaluating the at least one of strain and velocity measures for mechanical synchrony of the myocardial tissue within a given cardiac cycle and adjusting the variable timing parameters of the implantable stimulation device to increase mechanical synchrony of the patient's myocardial tissue in subsequent cardiac cycles. These and other objects and advantages of the invention will become more apparent from the following description taken in conjunction with the accompanying drawings.

DETAILED DESCRIPTION OF THE PREFERRED EMBODIMENTS

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
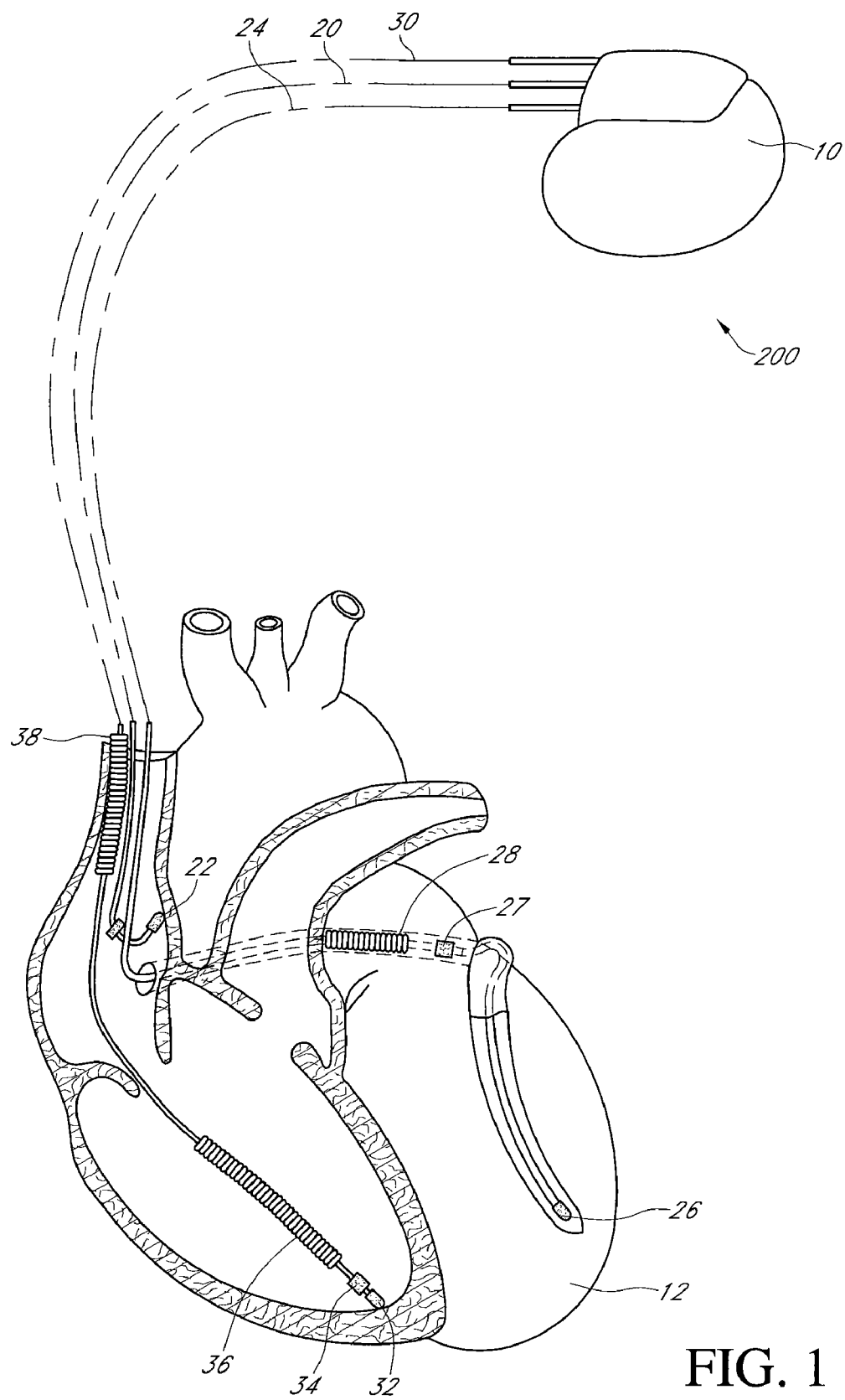
FIG. 1 is a simplified diagram illustrating an implantable stimulation device in electrical communication with at least three leads implanted into a patient's heart for delivering multi-chamber stimulation and shock therapy.

FIG. 1 illustrates one embodiment of an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
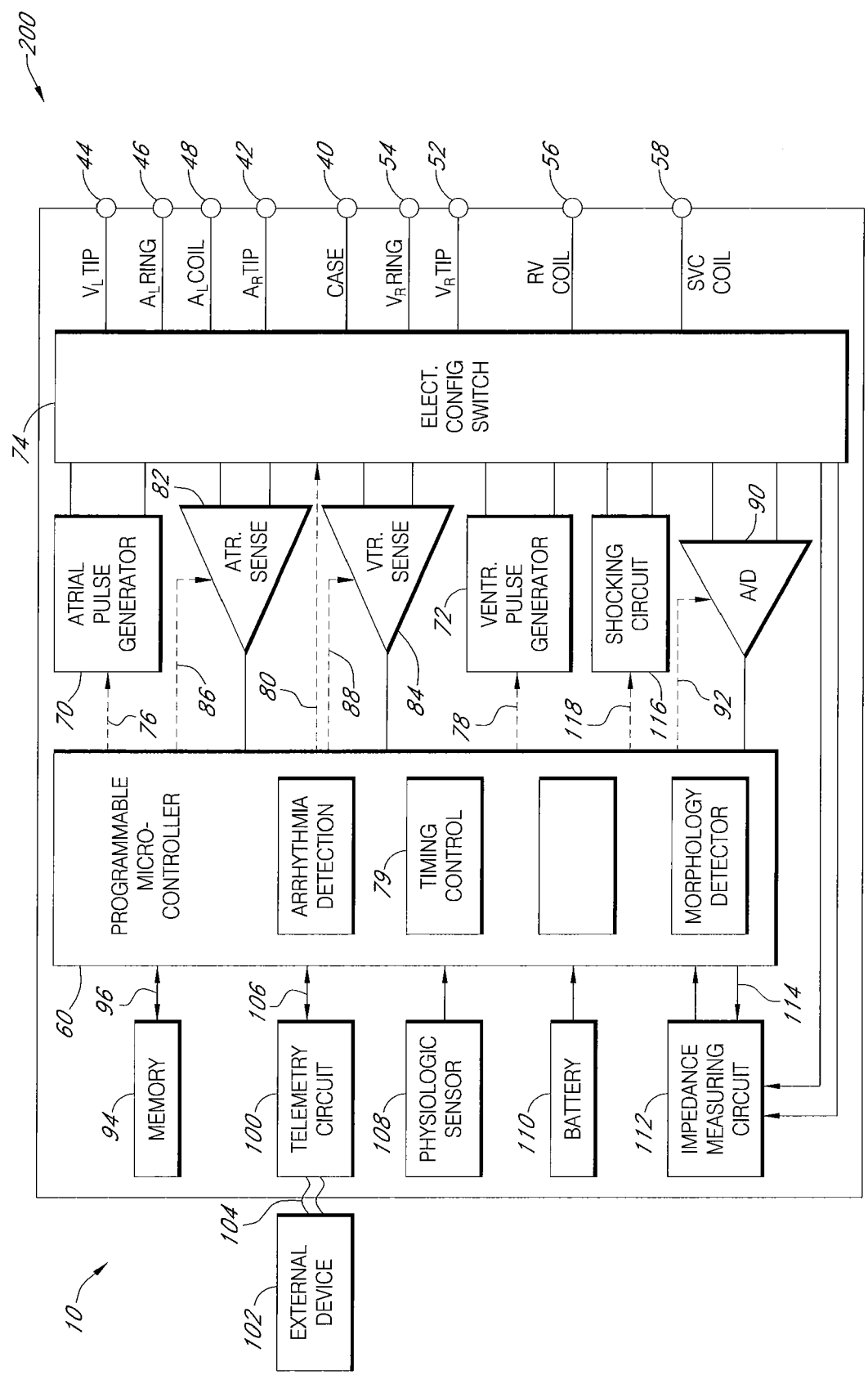
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monofluoride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
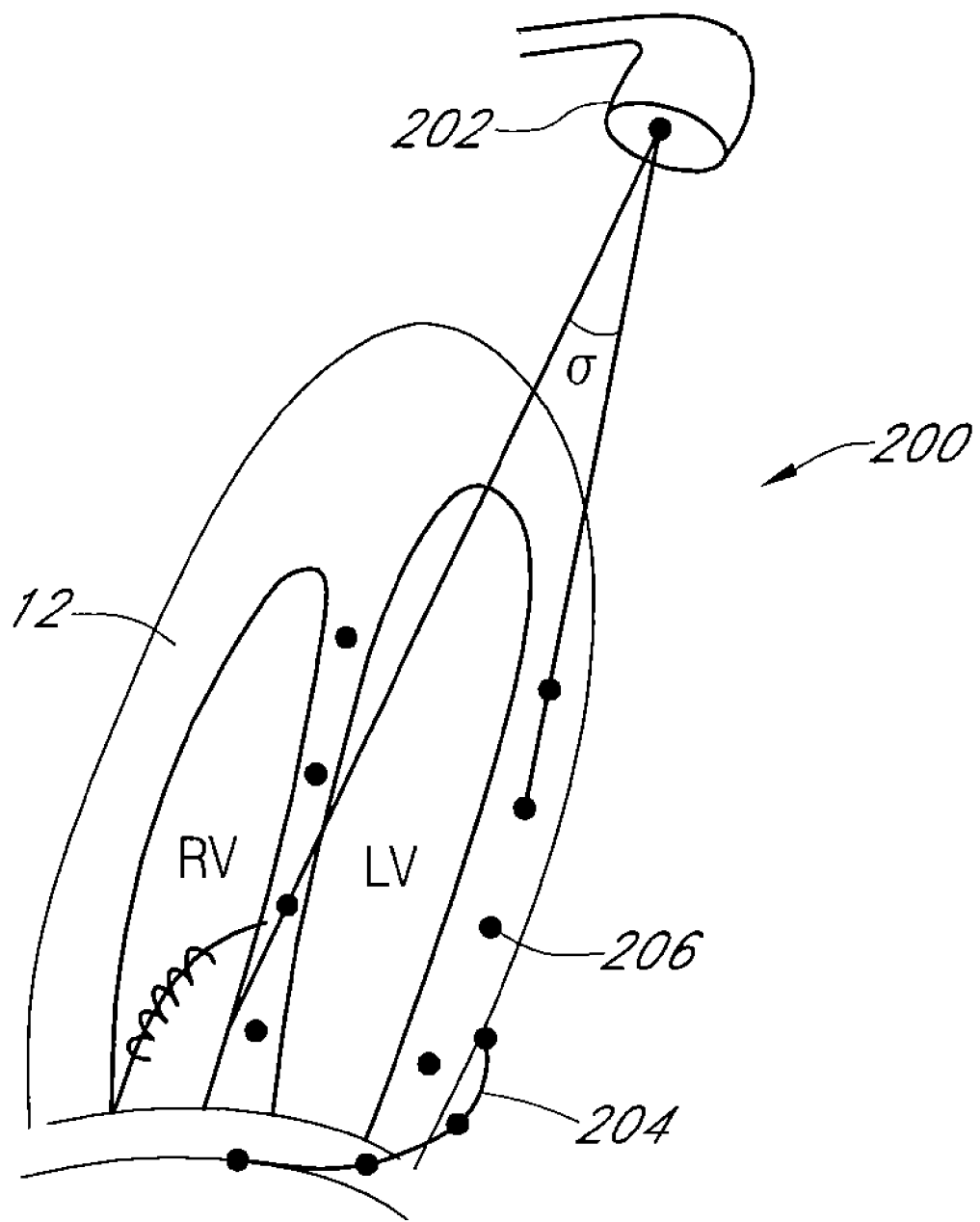
FIG. 3 illustrates one embodiment of a system for monitoring physiologic parameters of a patient, including in this embodiment both external and implanted measuring systems.

FIG. 3 illustrates schematically one embodiment of a therapy system 200 configured to measure and evaluate a patient's physiology and further adapted to assist adjustment of therapy delivery in an individualized manner to optimize the therapy for the needs and condition of the individual patient. As may be used herein, the terms "optimal", "optimize," "optimizing," "optimization", "minimize", "maximize" and the like are to be understood as commonly used terms of the art referring simply to a process of evaluating and adjusting or individualizing the operating parameters of a system for improved performance in an individual application. It will be understood that the physiologic activity and characteristics of an individual, for example their cardiac activity, is subject to both cyclical variations, diurnal variations, and long term variations.

An individual patient's physiologic activity can also be subject to variation brought about by medication dosing, environmental factors, and/or sensing noise which are generally asynchronous and unpredictable by an automated therapy system. Thus, the matching of therapy systems and methods to precise instantaneous needs of a patient is as a practical matter an inexact science. Thus, use of the terms "optimal", "optimize," "optimizing," "optimization" and the like does not imply that the described process results in a perfect setting for a system or method as used with an individual patient or that any further improvements are not available. Thus, the terms "optimize," "optimizing," and/or "optimization" are to be interpreted as relative terms indicating generally improved performance in an individual application and are not to be interpreted as absolutes.

In this embodiment, the system 200 includes one or more external measurement systems 202 and one or more measurement systems 204 adapted for internal measurements, e.g., from an implanted environment. In one embodiment, the external measurement system 202 includes an imaging system, such as an ultrasonic imager. In one particular embodiment, the external measurement system 202 generates and delivers ultrasonic vibrations which extend generally within a cone defined by an angle of ultrasonic insonification C). In this embodiment, the external measurement system 202 can direct the ultrasonic vibrations from an apical aspect of the patient's heart 12 to develop apical four chamber echocardiograph views of the patient's heart physiology.

In this embodiment, the system also includes one or more physiologic sensors 204 configured for internal sensing of the patient's physiology. In one embodiment, the internal sensors 204 include a multi-site coronary sinus (CS) lead and a right ventricular (RV) mid-basal septal lead. The internal sensing system 204 and the external measurement system 202 are adapted to measure activity and/or characteristics at regions of interest 206. FIG. 3 illustrates that in one embodiment the regions of interest 206 include various regions of the patient's heart 12, for example including septal and lateral wall regions.

In certain implementations, preferred locations for ventricular electrodes are adjacent the RV septum (Basal or High Septum) and the lateral LV wall via a bipolar CS lead. These locations provide data which is more congruent with data acquired ultrasonically, such as via the imager system 202. In other implementations, a preferred placement for RV leads is in the RV septal location. In other implementations, an electrode is preferably engaged with the septum with the RV coil electrode arranged in the RV apex. In yet other embodiments, RV apical leads can be used but may be less preferred.

FIG. 3 illustrates the regions of interest 206 schematically via solid black dots arranged at various locations of the patient's heart 12. It will be understood that in particular implementations, the regions of interest 206 would not constitute true points but would rather encompass a spatially extending volume or region of the patient's tissue. It will be further understood that the particular arrangement of the internal sensing system 204 as well as the measurements taken with one or more external sensing systems 202 would be adapted to the particular needs/concerns for the individual patient.

In certain embodiments, the system 200 facilitates analysis of mechanical parameters of physiologic activity such as tissue strain and/or velocity, for example obtained by the external sensing system 202. In one embodiment, an external sensing system 202 including an ultrasonic sensor is adapted to obtain physiologic data from regions of interest 206 arranged in the interventricular septum and LV lateral wall to provide valuable information for optimizing synchronization and for evaluation of the patient's condition. Data derived from the system 200 can also be utilized in more effectively interfacing external sensing systems and other external devices. Additional details of preferred embodiments of such interfacing and various systems and methods of measuring a patient's physiologic performance can be found in the co-owned U.S. patent application Ser. No. 11/748,894, filed May 15, 2007, of Dr. Stuart Schecter, entitled "MEDICAL EVALUATION AND THERAPY SYSTEM FOR OPTIMIZ- ING CARDIAC ELECTRO-MECHANICAL SYNCHRONY" which is incorporated herein in its entirety by reference.

In certain embodiments for purposes of optimizing resultant cardiac event timing, such as AV and RV-LV timing, structural physiologic data, such as acquired with ultrasonic measurements, is gathered while adjusting various interval timing parameters. Such measurement can be preferably performed over multiple cardiac cycles and the data gathered thereby further processed by summation averaging or ensemble averaging techniques to provide more representative data better accommodating for noise interference.

Figure 4:
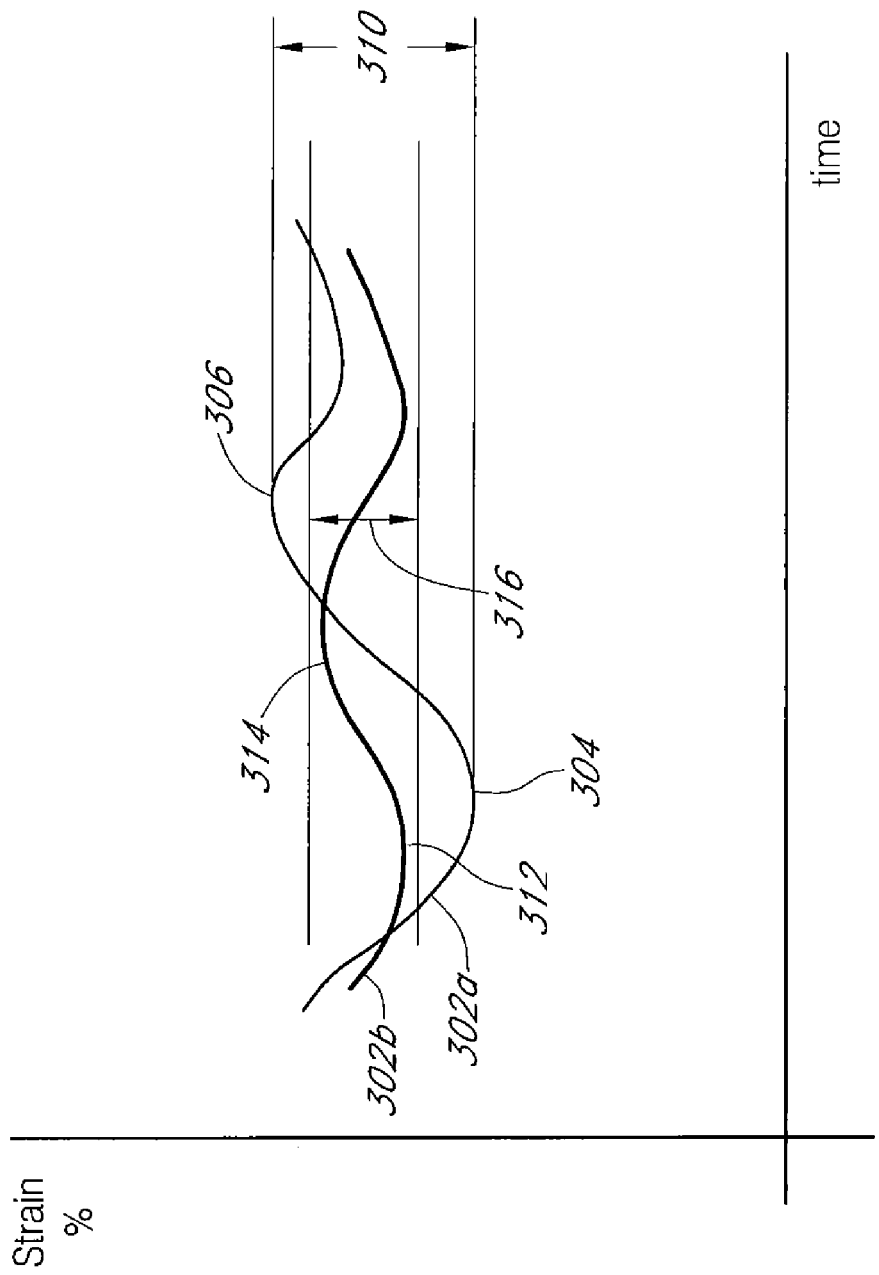
FIG. 4 illustrates exemplary strain waveforms corresponding to activity in more viable myocardial tissue and less viable myocardial tissue.

FIG. 4 illustrates one embodiment of mechanically-based measures of physiologic activity, in this embodiment corresponding to strain in percent over time and representing one cardiac cycle. Strain data is indicative of contractility and corresponds to local myocardial deformation along the spatial gradient being evaluated. Measurement of strain data can have limitations in certain applications as it generally requires contractility to exist in order for strain to be measured. For example, strain as a result of passive stretching may exist in nonviable tissue although strain generated in the opposite direction due to myocardial contractility will be limited in amplitude. The passive stretching is largely secondary to passive recoil and not related to intrinsic myocardial contractility. The peak-to-peak amplitude of a time varying strain signal will be reduced in tissue with reduced elasticity and will generally correlate with relative degree of myocardial fibrosis. Thus strain provides insight into the motion characteristics of heart tissue and can also provide indicators of less viable tissue.

FIG. 4 illustrates representative waveforms 302a and 302b indicative of strain measurements of different cardiac tissue, e.g., along different sensing vectors. The waveform 302a corresponds to more viable cardiac tissue. The waveform 302a exhibits a strain peak 304 corresponding generally to a local maximum of contractility and a peak 306 corresponding generally to local maxima diastolic relaxation. The waveform 302b is indicative of less viable tissue and exhibits a peak 312 associated generally with elastic recoil and a peak 314 associated generally with passive stretching.

In this embodiment, the waveform 302a exhibits a peak-to-peak amplitude indicated by the reference designator 310. In circumstances where limited myocardial liability exists, measurements of peak-to-peak strain may approach null. As such, in order to optimize synchrony in a multidimensional fashion, use of other indicators, such as myocardial velocity data, can be more appropriate. In one embodiment, a strain threshold indicated as the reference designator 316 is defined to establish a minimum peak-to-peak amplitude of a strain signal for use in evaluating the mechanical activity of the patient's heart. It will be understood that the particular value of a strain threshold 316 can be a programmable parameter and appropriately determined for the given patient and their particular condition. It will be further understood that as strain measurements can be performed along multiple spatial vectors encompassing different regions of cardiac tissue, different strain thresholds 316 can be defined for different sensing vectors.

Figure 5:
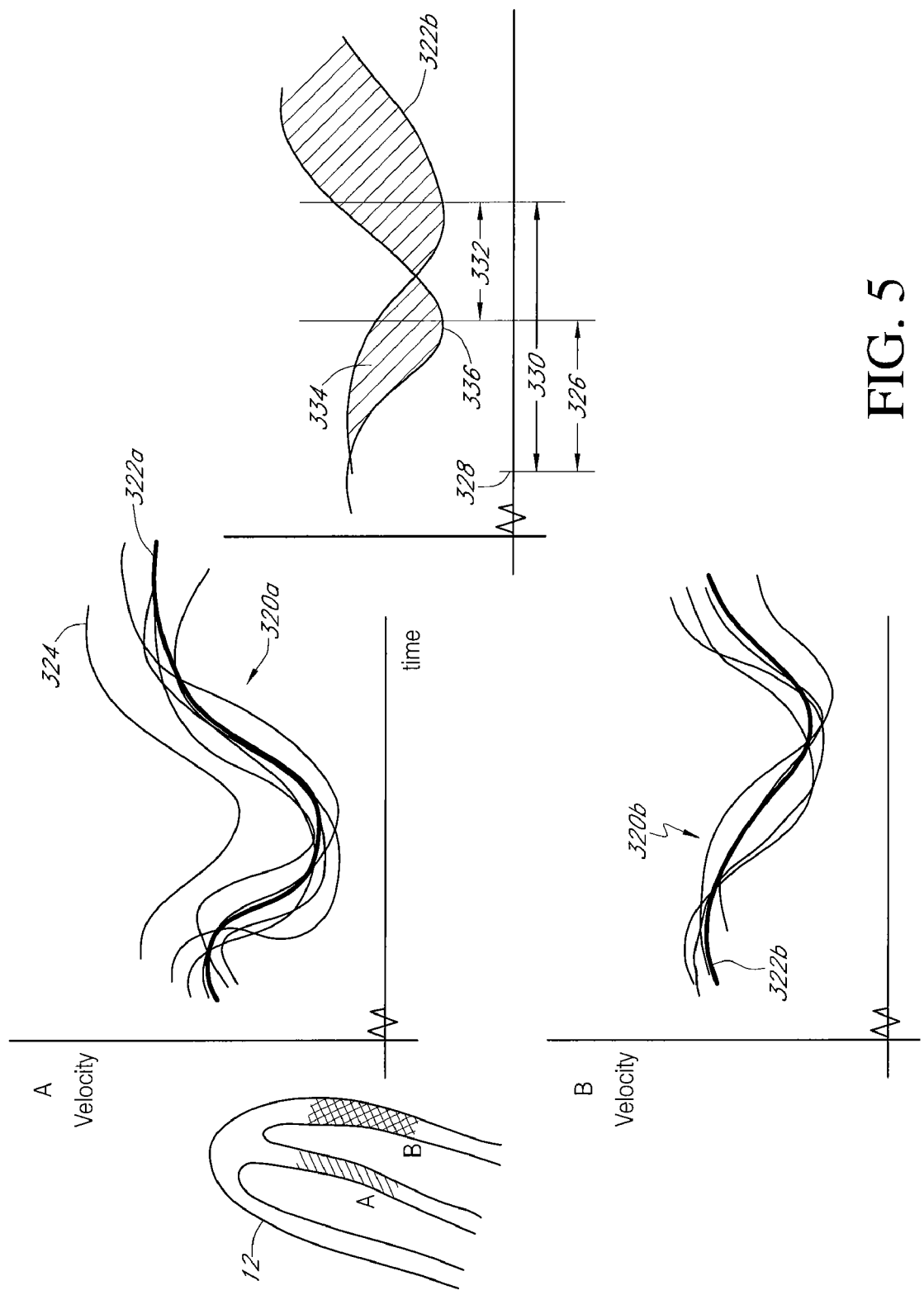
FIG. 5 illustrates exemplary waveforms of velocity waveforms indicative of tissue movement in different regions of a patient's heart.

FIG. 5 illustrates one embodiment of mechanically based measures of physiologic activity corresponding in this embodiment to velocity measurements over time. In this embodiment, velocity measurements are obtained generally for the midseptal region also indicated by the designator A of the patient's heart 12. Velocity measurements are also made generally of a lateral wall region indicated by the designator B.

In this embodiment, a plurality of velocity measurements are made for a corresponding plurality of cardiac cycles and are illustrated generally by the designator 320a. In this embodiment, the plurality of separate velocity measurements indicated in the waveforms 320a are ensemble averaged to generate a representative velocity waveform 322a. It will be understood that the representative velocity waveform 322a would generally not correspond precisely to any one single velocity measurement, however, is more generally representative, e.g., providing a characteristic or average indication of the physiologic activity. In this embodiment, at least one velocity measurement indicated by the designator 324 is not sufficiently homogeneous and is excluded form calculations resulting in the representative waveform 322a. As also illustrated in FIG. 5, similar waveforms of single cardiac cycles for the lateral wall region B are indicated by the waveforms 320b and an ensemble average resulting therefrom is indicated by the designator 322b.

FIG. 5 also illustrates the superposition of representative velocity waveforms 322a and 322b and several embodiments of timing and performance parameters that can be defined with respect thereto. In this embodiment, a first timing parameter 326 is defined which in this embodiment corresponds to the interval or time period from onset of the cardiac cycle 328 to peak velocity of the representative velocity waveform 322a corresponding to the midseptal region. A similar second timing interval 330 is defined corresponding to the time or duration from onset 328 to peak velocity for the representative velocity curve 322b indicative of lateral wall motion.

The difference between the first and second time intervals 326 and 330 is indicated by the reference designator 332. This difference can be considered as a velocity correction factor index (VCFI) 332. The velocity correction factor index 332 corresponds to the temporal disparity between occurrences of peak velocity in different regions of the patient's heart 12, in this exemplary illustration corresponding to the midseptal region and lateral wall region. Adjustment of delivered therapy to reduce the VCFI 332 towards zero will tend to unify or synchronize global myocardial velocities.

It should be understood that a VCFI 332 tending to zero will not necessarily result in simultaneous global unification or synchrony of strain or contractility. In certain implementations, acute benefits in the contractile state of the patient's myocardium are generally related to improvements in synchronization and diastolic filling to improve styling forces in predominantly viable myocardium rather than improvements in intrinsic contractility. Remodeling that takes place over time may in certain implementations be due in part to improvements in intrinsic contractility.

FIG. 5 also illustrates an integral difference 334 corresponding to the area of the region bounded inside the two representative velocity curves 332a and 330b over one cardiac cycle. Generally, a smaller value of the integral difference 334 will be associated with improved unification or synchrony of the velocity profiles of the respective regions of myocardium. In a similar manner to the VCFI 332, adjustment of therapy to reduce the integral difference 334 towards smaller values will generally achieve more complete unification or synchrony of the velocity characteristics of the patient's heart 12.

In certain embodiments, one or both of the VCFI 332 and integral difference 334 can be utilized as evaluation parameters for adjustment of therapy delivery, for example, including timing characteristics of therapy delivery to provide more effective therapy for the patient. In one embodiment, multiple data points where the integral difference 334 approaches a minimal value and similarly VCFI 332 approaches a minimal value can serve as abscissa and ordinate of a two-dimensional matrix for evaluation of a variable such as aortic velocity time integral (aortic VTI) or ejection fraction (EF) determinations. Further embodiments of a matrix based conceptualization of analyzing and selecting more optimal combinations of adjustable or variable parameters can be found in the co-owned U.S. patent application Ser. No. 11/556,552, filed Nov. 3, 2006, to Dr. Stuart Schecter, entitled "MATRIX OPTIMIZATION METHOD OF INDIVIDUALLY ADAPTING THERAPY IN AN IMPLANTABLE CARDIAC THERAPY DEVICE", which is incorporated herein in its entirety by reference.

Significant insights can be gained into myocardial viability by measuring and evaluating any differences between strain and velocity in various segments or regions of the myocardium. If a given region generates velocity during the cardiac cycle but reduced strain, this region is more likely to have scar tissue and less viability. The greater any differential between velocity and strain for this region, generally the less viability exists. Such data can be used to assess potential benefits of revascularization in a patient with significant velocity-strain mismatch. Evaluations of velocity strain mismatch can also be utilized with thallium redistribution studies and/or positron emission tomography (PET) can provide further insight into such conditions.

An integral difference between strain and myocardial velocity would yield useful data with respect to myocardial viability and could be used to determine the degree of velocity-strain mismatch. Summation or ensemble averaging of multiple strain and velocity curves over a particular homogenous segment of myocardium can be used to generate a single strain and single velocity curve as described above. An integral difference between these two curves would indicate myocardial viability in the examined region. If a marked difference existed between these curves, such a segment would have less viable tissue. A difficulty with this approach is, however, that velocity and strain are measured in different physical units, for example, meters per second and percent. For ease of calculation and data manipulation and evaluation, dimensionless indices can be preferable.

In one embodiment, dimensionless indices are defined and evaluated to evaluate velocity-strain mismatch. Analysis of the difference in peak maximal to peak minimal strain and velocity can be employed as a simplified analysis method. In order to provide dimensionless quantities, maximal and minimal values for each strain and velocity parameter can be divided to result in dimensionless values. In one embodiment, a strain quotient 340 is defined equal to peak maximum strain 306 divided by peak minimum strain 304. Similarly, a velocity quotient 345 can be defined equal to peak maximum velocity 338 divided by peak minimum velocity 336 (see FIGS. 4 and 5). The strain quotient 340 and velocity quotient 345 can be evaluated to result in a further strain-velocity index (SVI) 350 defined equal to the strain quotient 340 divided by the velocity quotient 345.

Figure 6:
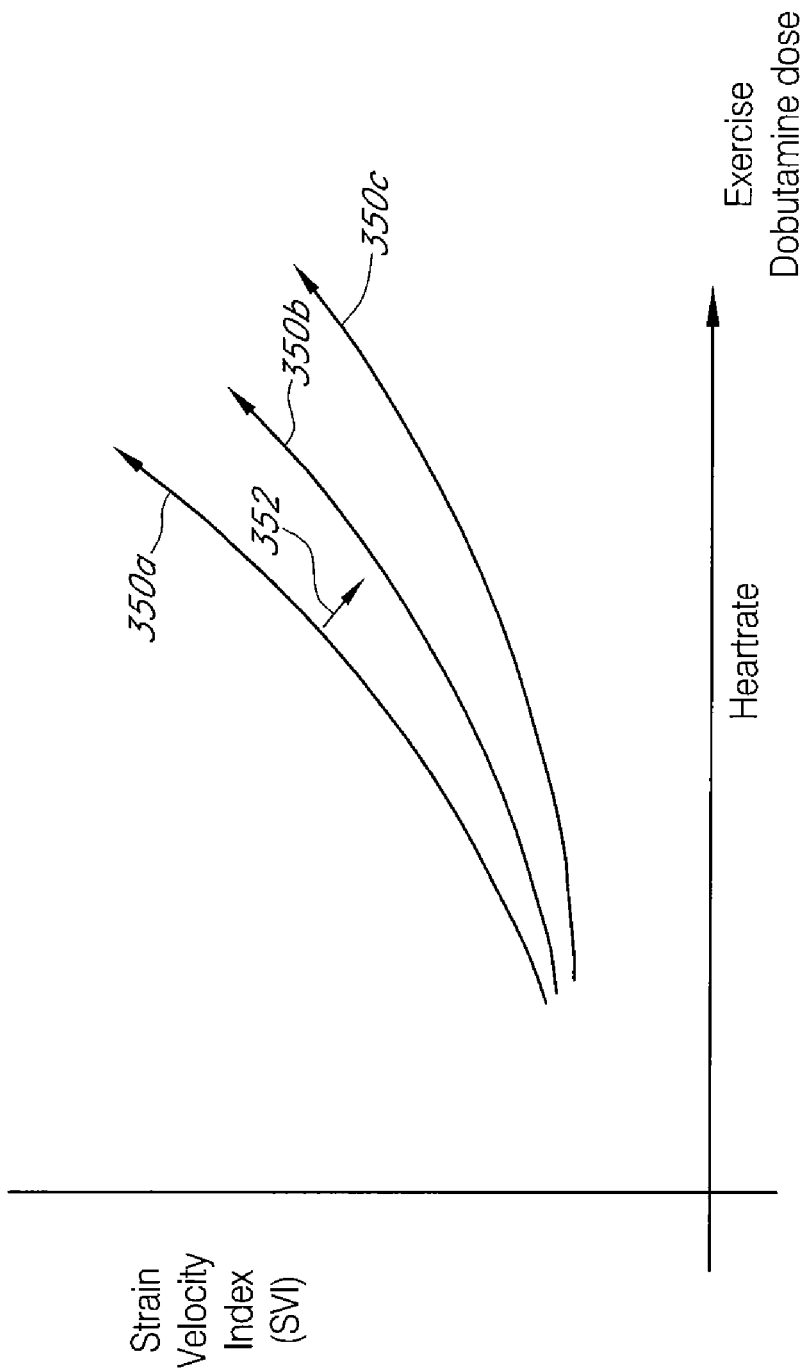
FIG. 6 illustrates one embodiment of a strain velocity index and various characteristics for varying heart rates and myocardial viability.

FIG. 6 illustrates schematically various strain-velocity indices 350 for varying heart rates. The varying heart rates could be due to varying exercise levels and/or Dobutamine provocation. A first SVI 350a indicates generally healthy strain-velocity relationships. A second SVI 350b indicates some reduced viability at least in the region analyzed and a third SVI 350c is indicative of more severe loss of viability at least in the region analyzed. The arrow indicated by the reference designator 352 indicates a direction of progressively reduced viability illustrated by a downward and rightward shift in the SVI curve.

As neighboring regions of interest can be expected to have different SVI 350 values indicating relative degrees of velocity-strain mismatch, these regions of interest can be characterized with ensemble averaging techniques as having a different degree of viability. This would be expected to be more relevant in ischemic heart disease as non-coronary cardiomyopathy is usually a globally homogeneous process. It can be further expected that there would be different etiologies to non-coronary cardiomyopathy, for example, hypertrophic cardiomyopathy, which may be determined at least in part by the characteristics of velocity and strain curve patterns as well as backscatter intensity and backscatter intensity over time, for example, over a cardiac cycle.

In certain embodiments, addition of ultrasonic backscatter intensity (UBI) to velocity and strain data can provide more clinically applicable data. For example, UBI can be utilized to further differentiate myocardial scar from tissue that is hibernating or stunned. Use of a mean UBI over a cardiac cycle as an additional variable can have incremental value in defining tissue properties. Analysis of UBI as a function of time, UBI(t)dt can also provide similarly valuable data. In one simplified implementation, relative disparities in UBI in specific myocardial segments can be evaluated with one or more measures of velocity strain mismatch.

Figure 7:
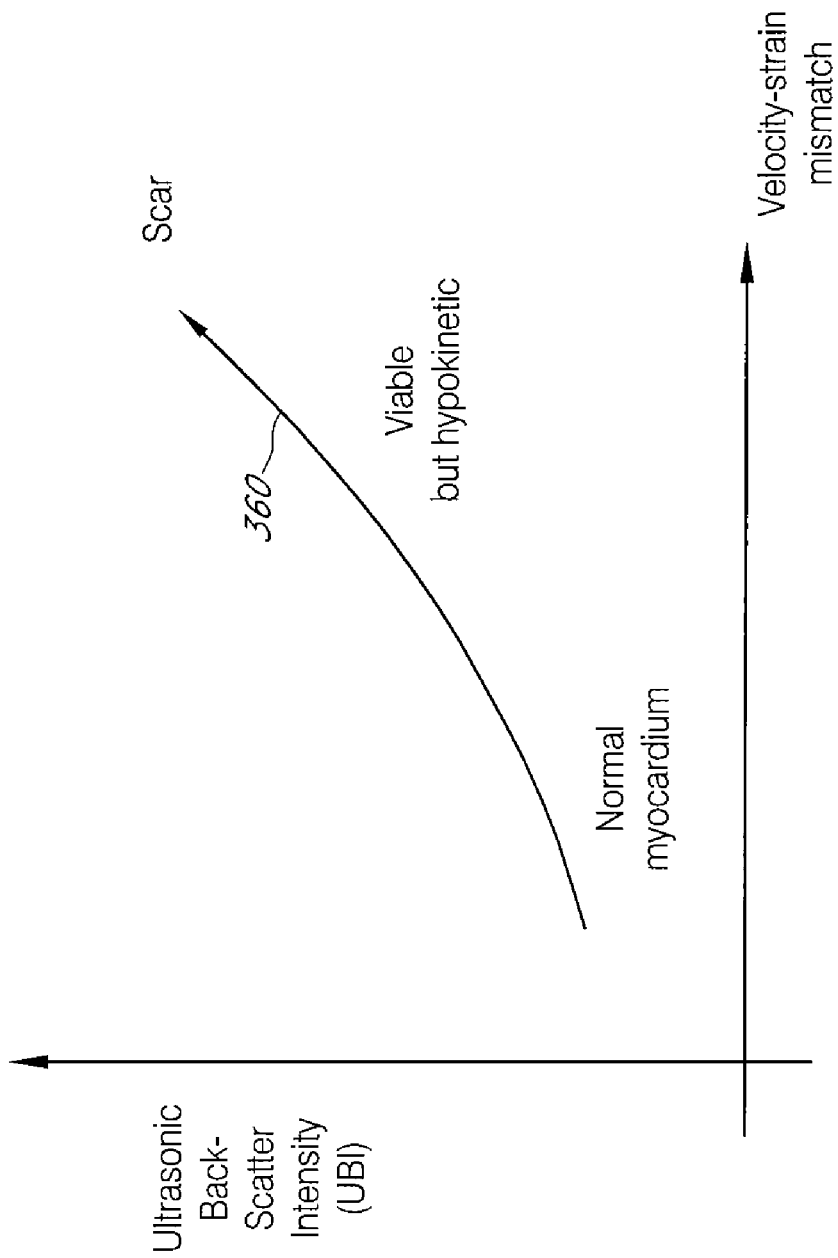
FIG. 7 illustrates one embodiment of a relationship between ultrasonic backscatter intensity and velocity-strain mismatch for varying levels of myocardial viability.

FIG. 7 provides a graphical representation of velocity-strain mismatch and UBI to define changes in myocardial segments at particular regions of interest, for example, in regions where infarct or peri-infarct ischemia may exist. Use of exercise stress and/or Dobutamine provocation while acquiring such data can assist in differentiation in certain implementations. For example, patients with non-coronary cardiomyopathy would be expected to exhibit relatively homogeneous levels of velocity strain mismatch similarly UBI(t)dt throughout substantially all myocardial segments. Degree of inhomogeneity will be indicative not only of those patients with ischemic heart disease but facilitate detection of territories having viability despite hypokinesis. In certain implementations, in order to obtain more clinically useful data, application of such velocity-strain mismatch and UBI data should be performed after cardiac resynchronization has been optimized.

Figure 8:
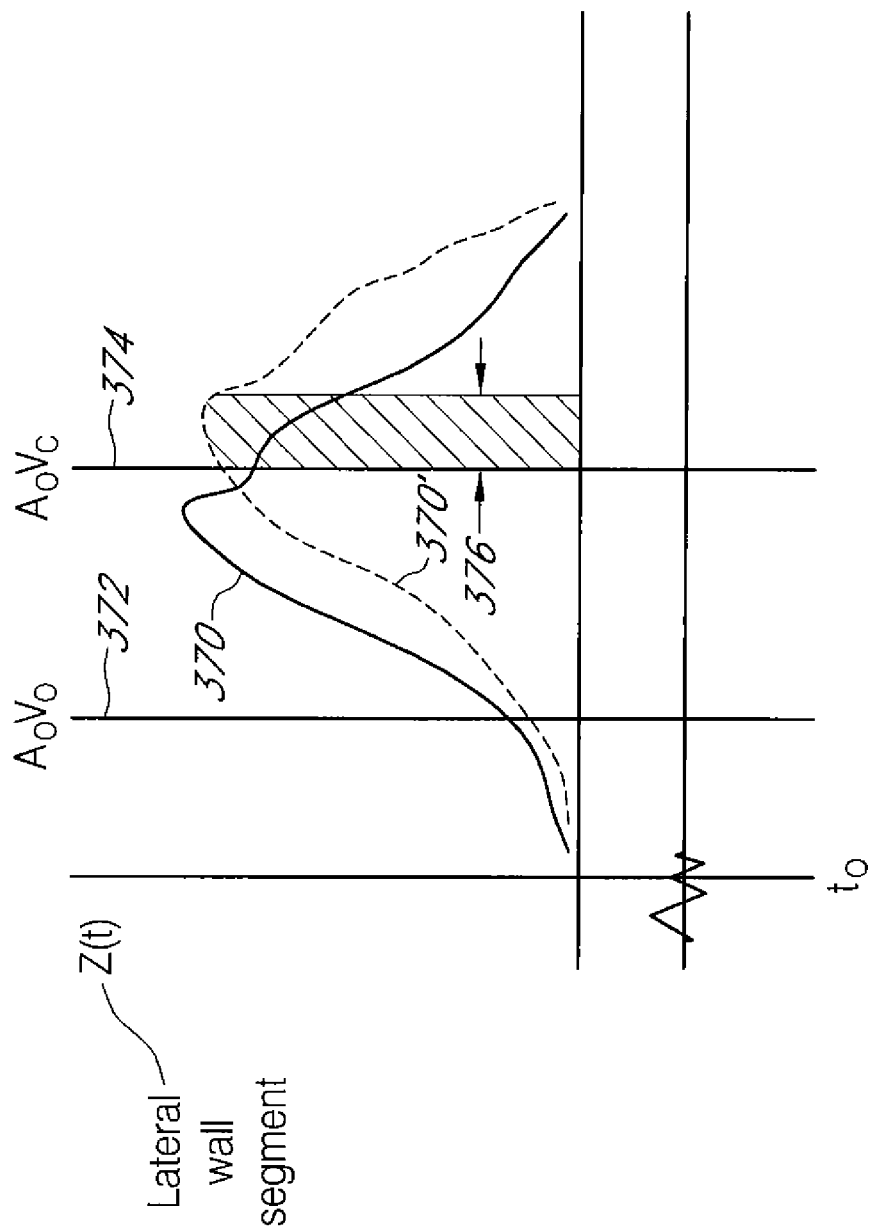
FIG. 8 shows one embodiment of impedance measurements as possible indicators of ischemia.

In certain embodiments, evaluation of intracardiac impedance data can be utilized in an analogous manner to ultrasonic strain and/or velocity measurements to determine and evaluate indications of myocardial ischemia. FIG. 8 illustrates an exemplary impedance waveform over a cardiac cycle indicating impedance measurements indicative of impedance characteristics of a lateral wall segment. The illustration of the intracardiac impedance waveform 370 is illustrated coincident with a marker or monument 372 indicating aortic valve opening and an indicator or monument 374 indicating aortic valve closure. In this embodiment, a second impedance waveform 370' is illustrated indicating impedance characteristics at elevated heart rates, for example, with exercise or Dobutamine provocation.

The elevated heart rate impedance waveform 370' exhibits an interval of post-systolic positive impedance (tPSPI) 376. The tPSPI 376 parameter can be monitored by the impedance circuit 114 of the implantable device 10 and instances or a history of the tPSPI 376 parameter can be stored. On office follow-up a clinician may notice that with increasing heart rate (e.g., decreasing RR intervals) the tPSPI 376 parameter increases. This would be indicative that the patient's myocardium, at least in this particular vector, may be jeopardized.

Another parameter that can be utilized to assess physiologic data can be defined in one embodiment as a post-systolic impedance index (PSZI). In one embodiment, the PSZI parameter is defined equal to $$\frac{Z(p) - Z(\text{ps})}{Z(\text{ps})}$$

where Z(p) is peak impedance and Z(ps) is peak systolic impedance. Monitoring of such data obtained via the implantable device 10 and particularly recorded data obtained therewith can serve to notify a clinician that an ischemic substrate may exist. Changes in these parameters prior to tachyarrhythmia therapy can at least partially define the etiology of clinical VT/VF in at least certain applications.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A therapeutic stimulation system comprising:
   an implantable cardiac stimulation device comprising:
   an implantable stimulation generator;
   at least one implantable lead adapted for connection to the implantable stimulation generator and further adapted for at least one of sensing physiologic activity and delivery of therapy;
   memory; and
   a controller in communication with the memory and with the at least one implantable lead and stimulation generator and configured to automatically evaluate a patient's physiologic status and selectively induce delivery of therapeutic stimulation under variable timing parameters; and
   an external measurement system comprising an ultrasonic imager adapted to measure at least one of strain and velocity of myocardial tissue and wherein the system is adapted to evaluate the at least one of strain and velocity measures and adjust the variable timing parameters of the implantable stimulation device to increase synchrony of the at least one of strain and velocity of myocardial tissue.

2. The system of claim 1, wherein the measurement system is adapted to measure strain and velocity of myocardial tissue and wherein the system is configured to compare a peak to peak amplitude of the strain to a strain threshold and to select velocity measurements to adjust the variable timing parameters of the implantable stimulation device to increase synchrony of velocity of myocardial tissue when the peak to peak amplitude of the strain does not exceed the strain threshold.

3. The system of claim 1, wherein the at least one measure of a patient's cardiac performance comprises a dimensionless index comprising a ratio of at least one of a first and a second strain measure and a first and a second strain velocity measure.

4. The system of claim 1, wherein the measurement system is adapted to measure at least one of strain and velocity of myocardial tissue at a plurality of regions of interest of a patient's heart and wherein the system is configured to determine areas bounded by at least one of strain and velocity signals over time for different regions of interest and to adjust the variable timing parameters of the implantable stimulation device to induce the areas toward zero.

5. The system of claim 1, wherein the measurement system is adapted to measure at least one of strain and velocity of myocardial tissue at a plurality of regions of interest of a patient's heart and wherein the system is configured to determine a temporal difference between peak values of the at least one of strain and velocity for different regions of interest and to adjust the variable timing parameters of the implantable stimulation device to induce the temporal difference toward zero.

6. The system of claim 1, wherein the measurement system is adapted to measure strain and velocity of myocardial tissue and wherein the system is configured to determine an index indicative of mismatch between strain and velocity.

7. The system of claim 6, wherein the measurement system is further adapted to measure ultrasonic backscatter intensity and wherein the system is further configured to evaluate the ultrasonic backscatter intensity and mismatch between strain and velocity and determine an indicator of myocardial viability.

8. The system of claim 1, wherein the measurement system is further adapted to monitor myocardial impedance and wherein the system evaluates the impedance and determines an indicator of ischemia when the system detects elevated post systolic positive values of the impedance at increased heart rates.

9. A therapeutic stimulation system comprising:
   an implantable cardiac stimulation device comprising:
   an implantable stimulation generator;
   at least one implantable lead adapted for connection to the implantable stimulation generator and further adapted for at least one of sensing physiologic activity and delivery of therapy;
   memory; and
   a controller in communication with the memory and with the at least one implantable lead and stimulation generator and configured to automatically evaluate a patient's physiologic status and selectively induce delivery of therapeutic stimulation under variable timing parameters; and
   a measurement system adapted to measure at least one of strain and velocity of myocardial tissue and wherein the system is adapted to evaluate the at least one of strain and velocity measures and adjust the variable timing parameters of the implantable stimulation device to increase synchrony of the at least one of strain and velocity of myocardial tissue, wherein the strain-velocity index is determined as peak maximum strain divided by peak minimum strain quantity divided by quantity peak maximum velocity divided by peak minimum velocity.

10. A method of adjusting therapy delivery in an implantable cardiac stimulation device, the method comprising:
    providing therapeutic cardiac stimulation to a patient via an implantable cardiac stimulation device operating under a set of variable timing parameters;
    measuring at least one of strain and velocity of the patient's myocardial tissue using an ultrasonic imager;
    evaluating the at least one of strain and velocity measures for mechanical synchrony of the myocardial tissue within a given cardiac cycle; and
    adjusting the variable timing parameters of the implantable stimulation device to increase mechanical synchrony of the patient's myocardial tissue in subsequent cardiac cycles.

11. The method of claim 10, comprising:
    measuring strain and velocity of myocardial tissue;
    comparing a peak to peak amplitude of the strain to a strain threshold; and selecting velocity measurements to adjust the variable timing parameters of the implantable stimulation device to increase synchrony of velocity of myocardial tissue for subsequent cardiac cycles when the peak to peak amplitude of the strain does not exceed the strain threshold.

12. The method of claim 10, comprising:
measuring at least one of strain and velocity of myocardial tissue at a plurality of regions of interest of the patient's heart;
determining areas bounded by at least one of strain and velocity signals over time for different regions of interest; and
adjusting the variable timing parameters of the implantable stimulation device to induce the areas toward zero.

13. The method of claim 10, comprising:
measuring at least one of strain and velocity of myocardial tissue at a plurality of regions of interest of the patient's heart;
determining a temporal difference between peak values of the at least one of strain and velocity for different regions of interest; and
adjusting the variable timing parameters of the implantable stimulation device to induce the temporal difference toward zero.

14. The method of claim 10, comprising:
measuring strain and velocity of myocardial tissue;
calculating a strain quotient of peak maximum strain divided by peak minimum strain;
calculating a velocity quotient of peak maximum velocity divided by peak minimum velocity; and
calculating a strain-velocity mismatch index equal to the quotient of the strain quotient and the velocity quotient as an indicator of myocardial viability.

15. The method of claim 14, further comprising:
measuring ultrasonic backscatter intensity; and
evaluating the ultrasonic backscatter intensity and the strain-velocity mismatch index to determine a further indicator of myocardial viability.

16. The method of claim 10, further comprising:
monitoring myocardial impedance;
evaluating the impedance at various heart rates; and
determining an indicator of ischemia when the system detects elevated post systolic positive values of the impedance at increased heart rates.

17. A method of adjusting therapy delivery in an implantable cardiac stimulation device, the method comprising:
providing therapeutic cardiac stimulation to a patient via an implantable cardiac stimulation device operating under a set of variable timing parameters;
measuring at least one of strain and velocity of the patient's myocardial tissue;
evaluating the at least one of strain and velocity measures for mechanical synchrony of the myocardial tissue within a given cardiac cycle;
adjusting the variable timing parameters of the implantable stimulation device to increase mechanical synchrony of the patient's myocardial tissue in subsequent cardiac cycles; and
calculating an index indicative of myocardial viability equivalent to at least one ratio of at least one of a first and a second strain measure and of a first and a second strain velocity measure.

* * * * *